(12) United States Patent
Tannhauser

(10) Patent No.: US 11,547,401 B2
(45) Date of Patent: Jan. 10, 2023

(54) SUTURE PACKAGES HAVING INTEGRATED SUTURE STRAIGHTENING ASSEMBLIES

(71) Applicant: Ethicon, Inc., Somerville, NJ (US)

(72) Inventor: Robert J. Tannhauser, Bridgewater, NJ (US)

(73) Assignee: Ethicon, Inc., Raritan, NJ (US)

(*) Notice: Subject to any disclaimer, the term of this patent is extended or adjusted under 35 U.S.C. 154(b) by 0 days.

(21) Appl. No.: 16/726,469

(22) Filed: Dec. 24, 2019

(65) Prior Publication Data

US 2021/0186491 A1 Jun. 24, 2021

(51) Int. Cl.
*A61B 17/06* (2006.01)

(52) U.S. Cl.
CPC .. *A61B 17/06133* (2013.01); *A61B 17/06061* (2013.01); *A61B 2017/06142* (2013.01)

(58) Field of Classification Search
CPC ........ A61B 17/06133; A61B 17/06061; A61B 2017/06142
USPC ................ 206/572, 366, 380, 382, 383, 339
See application file for complete search history.

(56) References Cited

U.S. PATENT DOCUMENTS

| | | | |
|---|---|---|---|
| 2,022,091 A | 5/1932 | Scharnhorst | |
| 2,517,309 A * | 8/1950 | Heller | B21F 1/02 72/162 |
| 3,196,656 A * | 7/1965 | Johnston | B21F 1/02 72/162 |
| 3,443,771 A | 5/1969 | Doty | |
| 3,749,238 A | 7/1973 | Taylor | |
| 3,972,418 A * | 8/1976 | Schuler | A61B 17/06133 206/63.3 |
| 4,034,850 A | 7/1977 | Mandel et al. | |
| 4,823,794 A | 4/1989 | Pierce | |
| 5,236,083 A | 8/1993 | Sobel et al. | |
| 5,669,490 A | 9/1997 | Colligan et al. | |
| 6,067,835 A | 5/2000 | Pollock | |
| 6,804,937 B2 | 10/2004 | Dey et al. | |
| 8,763,436 B2 * | 7/2014 | Knewtson | B21F 1/02 72/162 |
| 8,978,435 B2 * | 3/2015 | Viviroli | B65H 57/14 140/147 |

(Continued)

FOREIGN PATENT DOCUMENTS

EP 0608138 7/1994

*Primary Examiner* — Rafael A Ortiz
*Assistant Examiner* — Sanjidul Islam

(57) ABSTRACT

A suture package includes a suture housing having a tray with a suture channel, and at least one suture disposed on the suture housing, whereby the suture includes a suture thread disposed within the suture channel of the tray. The package includes a suture straightening assembly including a suture dispensing path for removing the suture thread from the suture housing. The suture straightening assembly includes a first suture thread straightening section configured to apply a first flexing force within a first plane upon the suture thread as the suture thread is drawn along the suture dispensing path, and a second suture thread straightening section configured to apply a second flexing force within a second plane upon the suture thread as the suture thread is drawn along the suture dispensing path. The first and second planes extend along axes that define an angle relative to one another.

23 Claims, 7 Drawing Sheets

(56) References Cited

U.S. PATENT DOCUMENTS

| | | | |
|---|---|---|---|
| 2004/0050131 A1* | 3/2004 | Militaru | B21D 3/04 |
| | | | 72/162 |
| 2004/0177594 A1* | 9/2004 | Dey | A61B 17/06133 |
| | | | 53/430 |
| 2004/0260344 A1 | 12/2004 | Lyons et al. | |
| 2009/0078332 A1 | 3/2009 | DeLallo | |
| 2012/0004672 A1* | 1/2012 | Giap | A61B 17/06133 |
| | | | 606/148 |
| 2012/0055828 A1* | 3/2012 | Kennedy | A61B 17/06133 |
| | | | 206/363 |

* cited by examiner

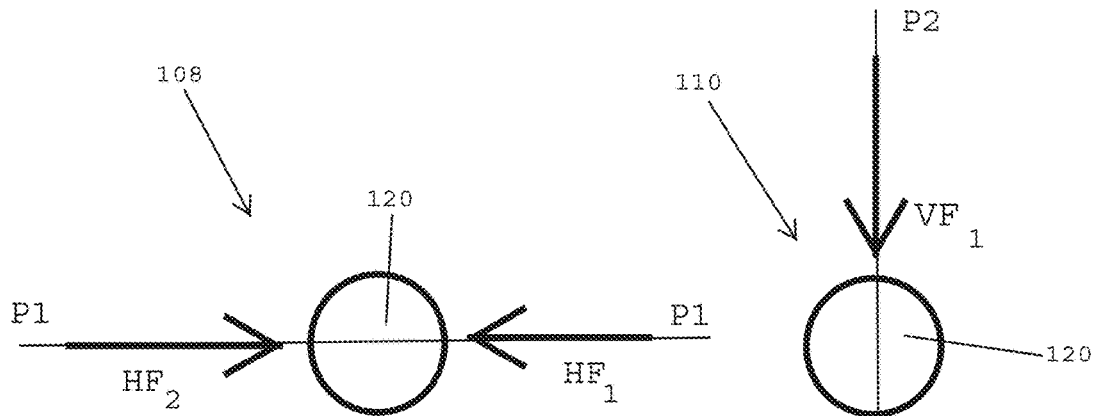
FIG. 9A
FIG. 9B
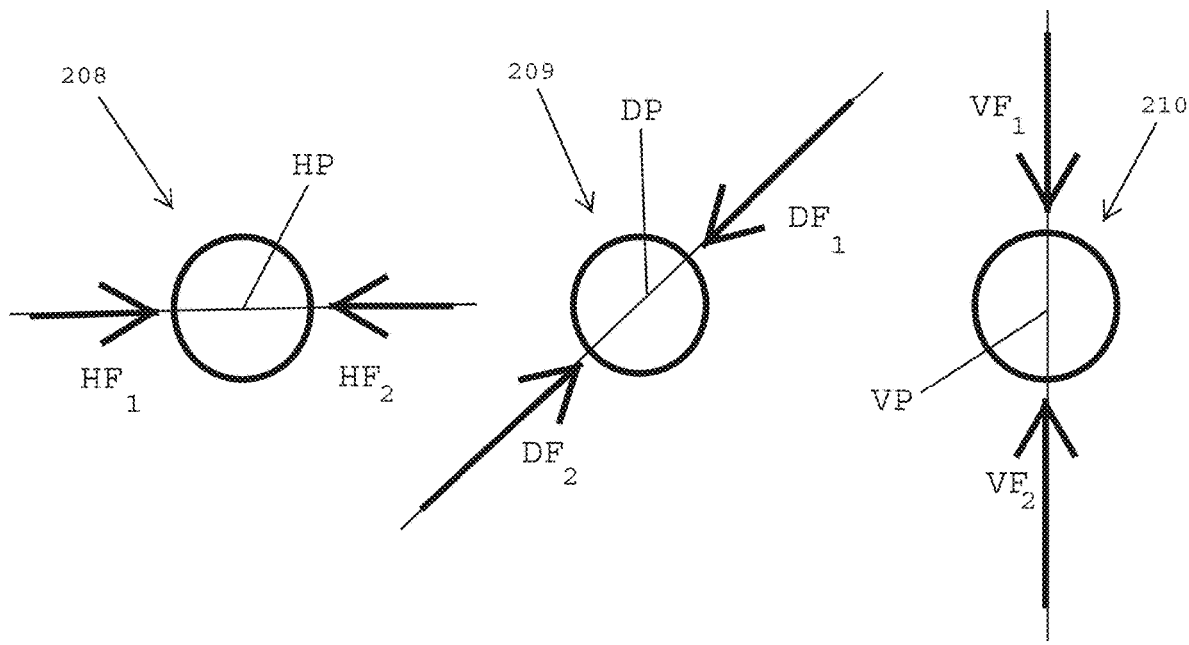
FIG. 10A
FIG. 10B
FIG. 10C

SUTURE PACKAGES HAVING INTEGRATED SUTURE STRAIGHTENING ASSEMBLIES

BACKGROUND OF THE INVENTION

Field of the Invention

The present patent application is generally related to medical devices, and is more specifically related to packages used to store sutures that are used during surgical procedures.

Description of the Related Art

Sutures are used during surgical procedures for closing wounds and surgical openings. A surgical needle (e.g., a curved suture needle) is secured to one end of a suture for providing an armed surgical needle that may be advanced through tissue.

Manual suturing is accomplished by using a needle driver to grab and hold the surgical needle, piercing tissue with a pointed end of the surgical needle, letting go of the surgical needle, and then re-grasping the surgical needle to pull the needle and the attached suture thread through the tissue being sutured.

Prior to being used in surgical procedures, sutures are often stored in suture packages that are designed to provide surgeons with sterile, undamaged sutures and surgical needles for use during surgical procedures. Suture packages are generally opened at surgical sites, whereupon the suture threads and surgical needles contained therein are removed from the packages for use in surgical procedures.

There are different suture packages that are used to store and deliver suture threads and surgical needles.

One type of suture package is a folder package, which has an array of flaps and panels that are folded about a suture or a plurality of sutures in order to secure the sutures inside the folder. Some folder packages have needle parks (e.g., a foam strip) that are secured to a panel for receiving and retaining surgical needles. Folder packages protect sutures during handling and shipping, and also allow for sterilization by enabling sterilizing gases to penetrate the folder package and reach the sutures.

Another type of package is a suture tray package, which typically includes a molded structure having tracks (e.g., suture channels) that receive sutures, and a needle park for anchoring suture needles to the package. Suture tray packages are relatively inexpensive to make, and may be used with high speed machinery in automated loading and packaging processes. An advantage of molded suture packages is the ease of dispensing sutures from the molded trays, which saves time during surgical procedures.

When suture threads are disposed within a suture package they are typically stored in coiled, curved or oval-shaped configurations in which the suture threads have a slight bend along the length of the suture to enable the suture to lay flat within the package. Some sutures take a set after being packaged. The set prevents the suture from being straight when dispensed from the package. Thus, the suture has bends. The set problem is particularly problematic with monofilament sutures that are exposed to heat as part of a sterilization process.

FIG. 1 shows a prior art suture package 50 having a suture channel 52 that is adapted to receive one or more suture threads 54. The one or more suture threads 54 are wound in an oval shaped configuration to form suture loops 56 that extend over the suture package 50. A surgical needle 58 is secured to a distal end of a suture thread 54 and is secured in a needle park 60 that is located at a top side of the suture package 50. The suture package 50 includes flaps 62 that are configured to swing away from the suture channel 52 for enabling the suture threads 54 to be loaded into the suture package 50.

In order to utilize the suture thread 54 during a surgical procedure, the surgical needle 58 is uncoupled from the needle park 60 and the suture thread is drawn from a passageway 64 of the suture package 50.

Referring to FIG. 2, due to the fact that the suture thread 54 was stored as a suture loop 56 within the suture channel 52 of the package, the suture thread takes a set after being packaged within the suture package 50. As a result, after the suture thread 54 is removed from the suture package 50, the suture thread contains a plurality of bends or loops 66A-66C. The presence of bends or loops along the length of the suture thread may make it difficult to utilize the suture thread 54 during a suturing procedure.

There have been some efforts directed to straightening sutures when they are removed from suture packages. For example, US 2012/0004672 to Giap et al, discloses a suture straightening device that is designed to straighten strands of suturing material that have been wound upon a storage component. The suture straightening device, which is positioned on the body of a suture and needle holder, includes an elongated soft member having a resilience which allows for a suture or suture-needle combination to be drawn through it during detachment of the needle and suture material from the storage component. During dismount of the needle and suturing material for use on the patient, the strand of suture material trailing from an attachment to the needle, is drawn through the elongated, pliable body member of the device. Pressure from the pliable member itself, or imparted to the pliable member by the user, is communicated to the strand of sliding suture material being drawn through the member. The pressure and the sliding frictional engagement of the strand of suture material through the pliable body generates uniform tension that is imparted to the suture strand to stretch and realign the material forming the strand of the suture to remove the memorized shape imparted to the strand. The user is left with a substantially straight strand of suture material hanging from the needle, devoid of bends, loops, or coils.

The device disclosed in Giap et al. only flexes the suture in one plane. Thus, there is a continuing need for suture packages having suture straightening assemblies that flex a suture in multiple planes as the suture thread is removed from a suture package for providing a straightened suture that may be used during suturing operations.

SUMMARY OF THE INVENTION

In one embodiment, a suture package preferably includes a suture straightening assembly having a suture dispensing path for dispensing suture threads from the suture package. As a suture thread is drawn and/or pulled through the suture straightening assembly, the suture straightening assembly preferably flexes the suture in different directions, preferably opposite to the direction of the "set" caused by storing the suture thread in the package. The suture dispensing path is preferably configured to reverse the "set" as the suture is dispensed from the package.

The suture dispensing path provided for dispensing the suture preferably flexes the suture in at least one direction. In one embodiment, the flexing will take place in two opposing directions. In another embodiment, the flexing of the suture thread will be in more than one pair of opposing directions (i.e., in multiple planes). This is especially important when dispensing sutures that take on a "set" having a slight bend or loop in their coiled configurations.

In one embodiment, a suture package preferably includes a suture housing, and at least one suture disposed on the suture housing. The suture desirably includes a suture thread and a needle secured to an end of the suture thread. In one embodiment, the suture housing desirably includes a tray with a suture channel for the suture thread and a needle park that engages the needle for securing the needle to the tray. In one embodiment, the suture package may contain a plurality of sutures.

In one embodiment, the suture package desirably includes a suture straightening assembly provided on the suture housing. The suture straightening assembly preferably defines a suture dispensing path for removing the sutures from the suture housing.

In one embodiment, the suture straightening assembly preferably includes a first straightening section that is configured to apply first flexing forces upon an exterior surface of a suture thread within a first plane as the suture thread is drawn along the suture dispensing path.

In one embodiment, the suture straightening assembly preferably includes a second straightening section that is configured to apply second flexing forces upon the exterior surface of the suture thread within a second plane as the suture thread is drawn along the suture dispensing path.

In one embodiment, the first and second planes of the respective first and second straightening sections may extend along axes that define an angle relative to one another. In one embodiment, the first and second planes are perpendicular to one another. In one embodiment, one of the first and second planes is a horizontal plane and the other of the first and second planes is a vertical plane.

In one embodiment, the first straightening section preferably includes a first set of rollers that is configured to apply the first flexing forces upon the exterior surface of the suture thread within the first plane as the suture thread is drawn along the suture dispensing path.

In one embodiment, the first set of rollers includes two or more rollers on a first lateral side of the suture dispensing path, and one or more rollers on a second lateral side of the suture dispensing path that oppose the two or more rollers on the first lateral side of the suture dispensing path.

In one embodiment, the second straightening section preferably includes a second set of rollers that is configured to apply the second flexing forces upon the exterior surface of the suture thread within the second plane as the suture thread is drawn along the suture dispensing path.

In one embodiment, the second set of rollers includes two or more rollers above the suture dispensing path, and one or more rollers below the suture dispensing path that oppose the two or more rollers above the suture dispensing path.

In one embodiment, the suture straightening assembly is mounted on the suture housing of the suture package and has a suture thread inlet and a suture thread outlet. In one embodiment, the first and second suture straightening sections are located between the suture thread inlet and the suture thread outlet of the suture straightening assembly.

In one embodiment, the first and second sets of rollers of the respective first and second suture straightening sections are adjacent one another within the suture straightening assembly.

In one embodiment, the first set of rollers is closer to the suture thread inlet of the suture straightening assembly than the second set of rollers.

In one embodiment, the first set of rollers is closer to the suture thread outlet of the suture straightening assembly than the second set of rollers.

In one embodiment, the first set of rollers is mounted on a first carriage that aligns the rollers of the first set of rollers with the first plane, and the second set of rollers is mounted on a second carriage that aligns the rollers of the second set of rollers with the second plane.

In one embodiment, a suture package desirably includes a suture housing with a tray having a suture channel, and a plurality of sutures disposed on the suture housing, whereby each suture includes a suture thread disposed within the suture channel of the tray.

In one embodiment, the suture package preferably includes a suture straightening assembly provided on the suture housing. The suture straightening assembly desirably defines a suture dispensing path for removing the suture threads from the suture housing.

In one embodiment, the suture straightening assembly preferably has a first suture thread straightening section that is configured to apply first flexing forces within a first plane upon an exterior surface of the suture thread as the suture thread is drawn along the suture dispensing path, and a second suture thread straightening section that is configured to apply second flexing forces within a second plane upon the exterior surface of the suture thread as the suture thread is drawn along the suture dispensing path, whereby the first and second planes extend along axes that define an angle relative to one another.

In one embodiment, the first suture thread straightening section preferably includes a first set of rollers that is configured to apply the first flexing forces within the first plane upon the exterior surface of the suture thread as the suture thread is drawn along the suture dispensing path.

In one embodiment, the second suture thread straightening section preferably includes a second set of rollers that is configured to apply second flexing forces within the second plane upon the exterior surface of the suture thread as the suture thread is drawn along the suture dispensing path. In one embodiment, the first and second planes desirably extend along axes that define an angle relative to one another.

In one embodiment, the first flexing forces applied by the first suture straightening section (e.g., a first set of rollers) flexes the suture thread in two opposite directions within the first plane, and the second flexing forces applied by the second suture straightening section (e.g., a second set of rollers) flexes the suture thread in two opposite directions within the second plane.

In one embodiment, the first set of rollers desirably includes two or more rollers on a first lateral side of the suture dispensing path, and one or more rollers on a second lateral side of the suture dispensing path that oppose the two or more rollers on the first lateral side of the suture dispensing path.

In one embodiment, the second set of rollers preferably includes two or more rollers above the suture dispensing path, and one or more rollers below the suture dispensing path that oppose the two or more rollers above the suture dispensing path.

In one embodiment, a suture package includes two or more suture threads disposed within the suture channel, whereby the suture threads have a curved configuration when stored in the package. In one embodiment, each suture includes a needle secured to an end of one of the suture threads. In one embodiment, the tray preferably includes a needle park for securing the needles to the suture housing.

In one embodiment, a suture package preferably includes a suture housing with a tray having a suture channel and a needle park, and one or more sutures disposed on the suture housing, whereby each suture includes a suture thread disposed within the suture channel of the tray and a needle secured to an end of the suture thread that is secured to the tray at the needle park.

In one embodiment, the suture package preferably includes a suture straightening assembly provided on the suture housing, whereby the suture straightening assembly defines a suture dispensing path for removing a suture thread from the tray of the suture housing.

In one embodiment, the suture straightening assembly preferably includes a first suture thread straightening section (e.g., a first set of rollers) that is configured to apply first flexing forces within a first plane upon an exterior surface of the suture thread as the suture thread is drawn along the suture dispensing path, and a second suture thread straightening section (e.g., a second set of rollers) that is configured to apply second flexing forces within a second plane upon the exterior surface of the suture thread as the suture thread is drawn along the suture dispensing path. In one embodiment, the first and second suture thread straightening sections are desirably adjacent one another within the suture straightening assembly. In one embodiment, the first and second planes desirably extend along axes that define an angle (e.g., a 90 degree angle) relative to one another.

In one embodiment, one of the first and second planes is a horizontal plane and the other one of the first and second planes is a vertical plane that is perpendicular to the horizontal plane.

In one embodiment, the first flexing forces applied by the first suture thread straightening section flexes the suture thread in two opposite directions within the first plane, and the second flexing forces applied by the second suture thread straightening section flexes the suture thread in two opposite directions within the second plane.

In one embodiment, a suture straightening assembly may include a third suture thread straightening section (e.g., a third set of rollers) that flexes the suture thread in two opposite directions within a third plane, that defines a first angle with the first plane and a different, second angle with the second plane. In one embodiment, the first plane may be a horizontal plane, the second plane may be a vertical plane, and the third plane may be a diagonally extending plane that defines an angle of about 45 degrees with the respective first and second planes.

These and other preferred embodiments of the present invention will be described in more detail below.

BRIEF DESCRIPTION OF THE DRAWINGS

FIG. 9A illustrates flexing forces applied to lateral sides of a suture thread at the first section of the suture straightening assembly shown in FIG. 4.

FIG. 9B illustrates flexing forces applied to top and bottom sides of a suture thread at the second section of the suture straightening assembly shown in FIG. 4.

FIG. 10A illustrates flexing forces applied by a suture straightening assembly within a first plane to a suture thread, in accordance with one embodiment of the present patent application.

FIG. 10B illustrates flexing forces applied by a suture straightening assembly within a second plane to a suture thread, in accordance with one embodiment of the present patent application.

FIG. 10C illustrates flexing forces applied by a suture straightening assembly within a third plane to a suture thread, in accordance with one embodiment of the present patent application.

DETAILED DESCRIPTION OF PREFERRED EMBODIMENTS

Figure 1:
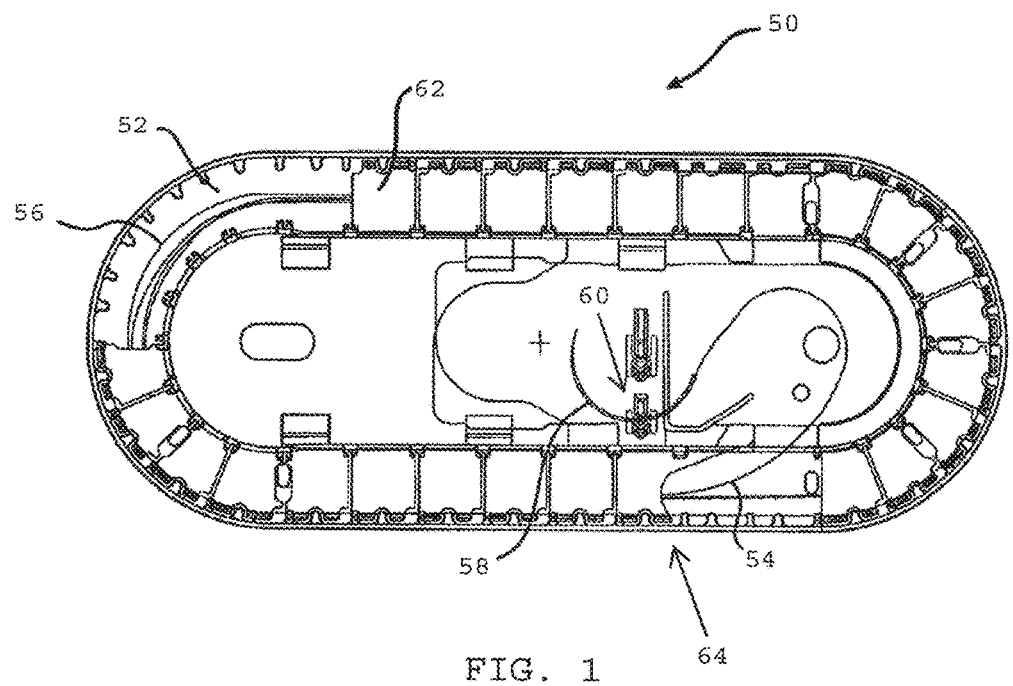
FIG. 1 is a top plan view of a prior art suture package.
Figure 2:
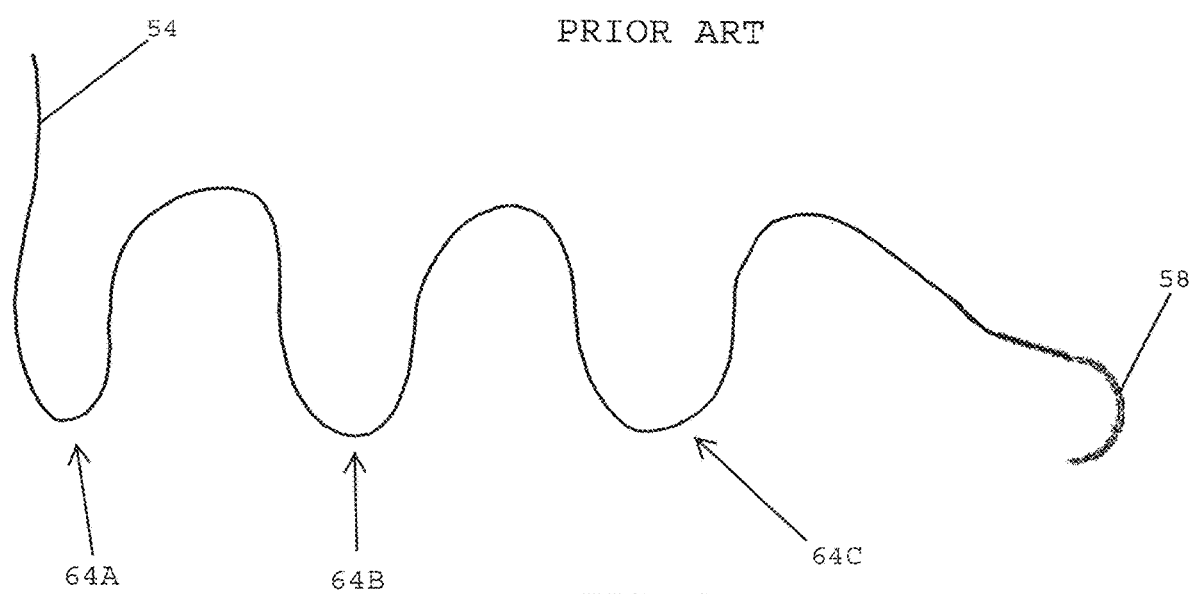
FIG. 2 is a side view of a suture that has been removed from the prior art suture package shown in FIG. 1.
Figure 3:
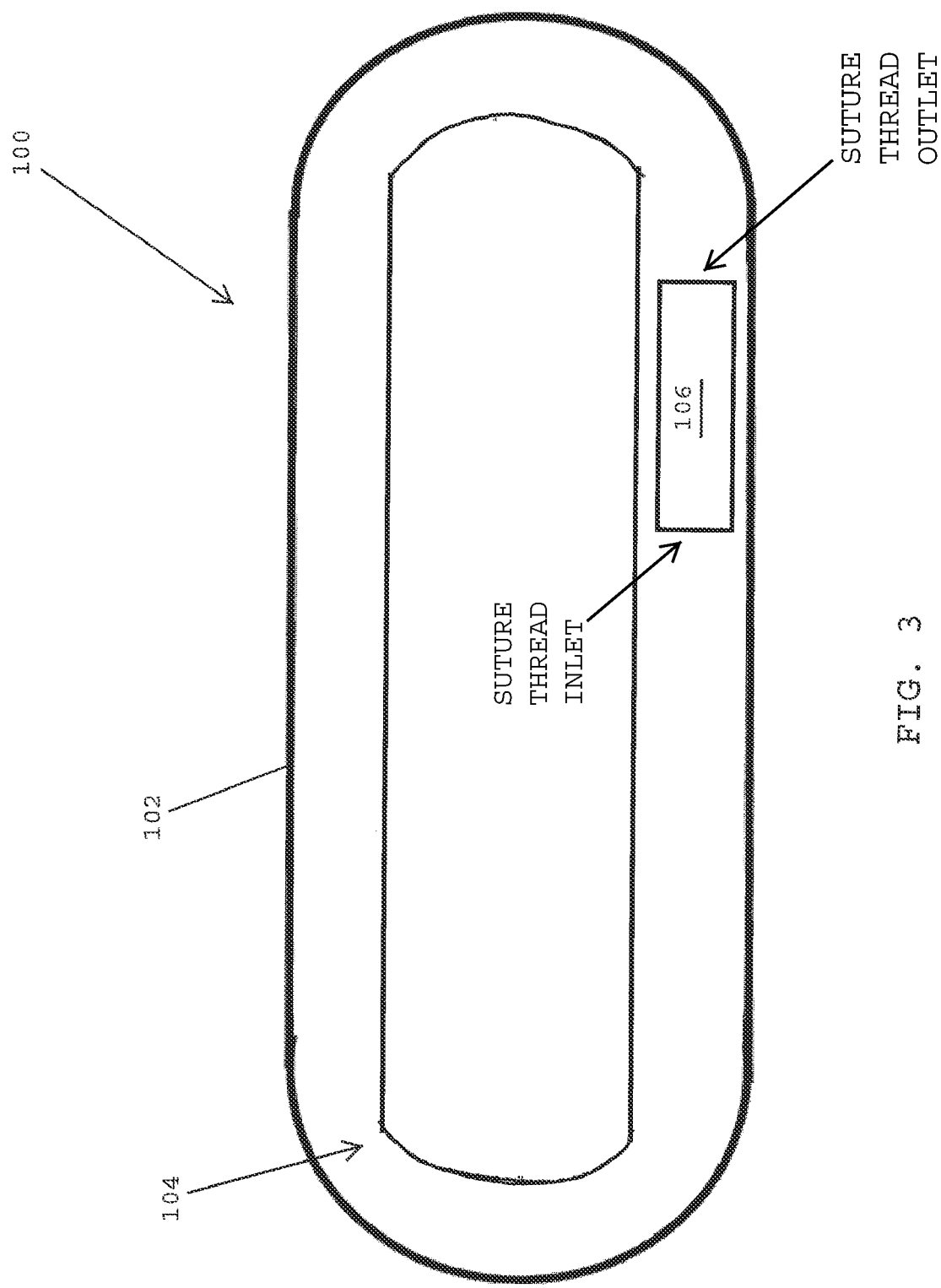
FIG. 3 is a schematic view of a suture package including a suture straightening assembly, in accordance with one embodiment of the present patent application.

Referring to FIG. 3, in one embodiment, a suture package 100 preferably includes a tray 102 having a suture channel 104 provided thereon. The suture channel 104 is configured to receive one or more flexible suture threads of a suture. In one embodiment, the suture threads may be stored in a circular or oval configuration to provide one or more suture loops within the suture channel 104, which extend around the perimeter of the tray 102 of the suture package 100. In one embodiment, the sutures threads may be monofilament sutures that are exposed to heat as part of a sterilization process.

In one embodiment, the suture package 100 preferably includes a suture straightening assembly 106 provided thereon. In one embodiment, the suture straightening assembly 106 is configured to straighten a suture thread as it is drawn through the suture straightening assembly 106. In one embodiment, as a suture is removed from the package 100 for performing a suturing operation, the suture thread, preferably secured to a needle, is drawn through the suture straightening assembly for straightening the suture thread to remove any bends or loops that may be present in the suture thread. In one embodiment, the suture straightening assembly 106 may be located at an area of the suture package where the suture thread is dispensed from the suture package.

The suture package 100 shown in FIG. 3 may have one or more of the features disclosed in commonly assigned U.S. Pat. Nos. 6,644,469 and 6,804,937, both assigned to Ethicon, Inc. of Somerville, N.J., the disclosures of which are hereby incorporated by reference herein.

In one embodiment the suture material (e.g., the suture thread) may be made of conventional, biocompatible, absorbable materials, non-absorbable materials, and combinations of absorbable and non-absorbable materials. Preferred non-absorbable materials include polypropylene, a polymer blend of polyvinylidene fluoride and polyvinylidene fluoride-co-hexafluoropropylene, polyethylene, polyvinylidene fluoride (PVDF), polyesters, polyethylene terephthalate, glycol-modified polyethylene terephthalate, polytetrafluoroethylene, fluoropolymers, nylons etc. and the like, or copolymers of combinations thereof. Preferred absorbable polymeric materials include polydioxanone, polyglactin, polyglycolic acid, copolymers of glycolide and lactide, polyoxaesters, and poliglecaprone. In certain preferred embodiments, the suture material may include combinations of both absorbable and non-absorbable materials. In one preferred embodiment, the suture material preferably includes a polymer blend of polyvinylidene fluoride and polyvinylidene fluoride-co-hexafluoropropylene material. In addition, any of these materials may have conventional surface modifications that include coatings, plasma treatments, therapeutics, and the like. In one embodiment, the needle 58 is coated with a silicon coating. In one embodiment, the suture 54 is a polypropylene suture sold under the trademark PROLENE® polypropylene suture by Ethicon, Inc of Somerville, N.J.

Figure 4:
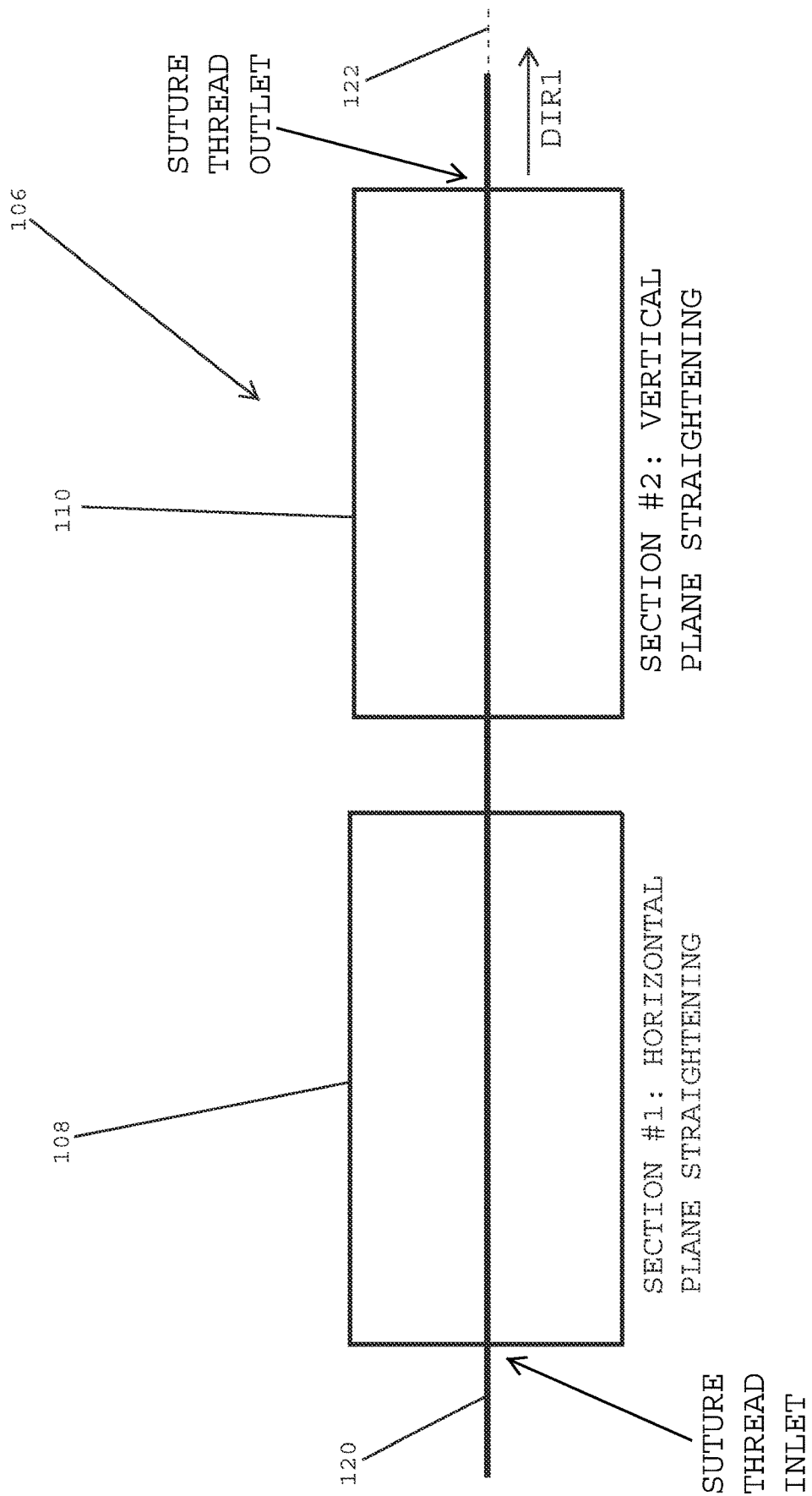
FIG. 4 is a schematic view of a suture straightening assembly including a first section that flexes a suture thread in a first plane and a second section that flexes a suture thread in a second plane, in accordance with one embodiment of the present patent application.

Referring to FIG. 4, in one embodiment, the suture straightening assembly 106 preferably includes a first straightening section 108 (e.g., a horizontal straightening section) that is configured to straighten a suture thread within a first plane, and a second straightening section 110 (e.g., a vertical straightening section), adjacent the first straightening section 108, that is configured to straighten a suture thread within a second plane.

Figure 5:
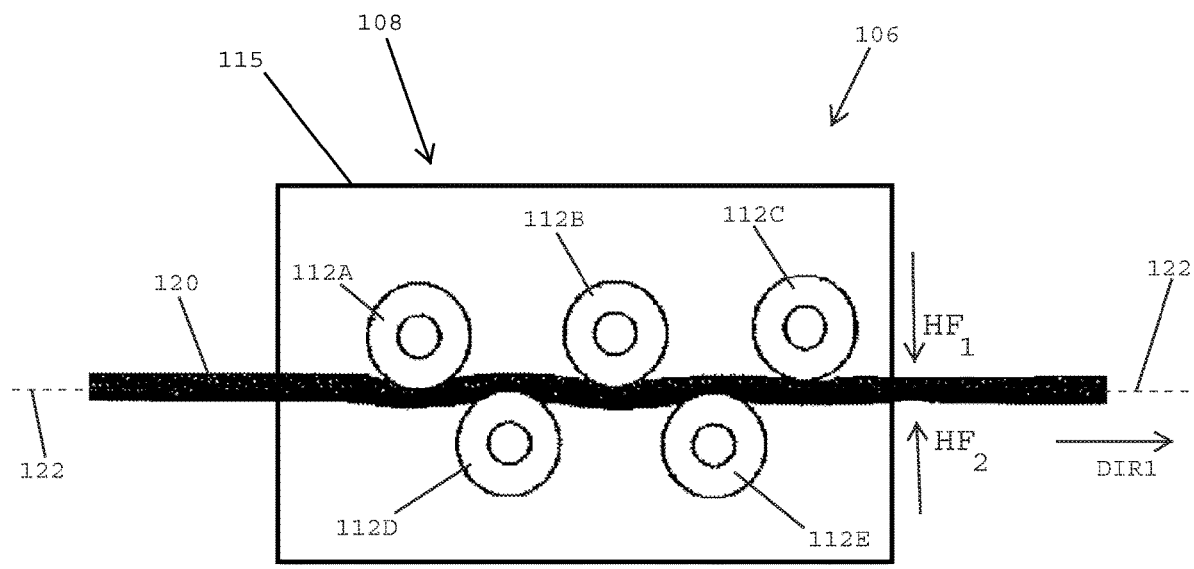
FIG. 5 is a top plan view of the first section of the suture straightening assembly shown in FIG. 4.
Figure 6:
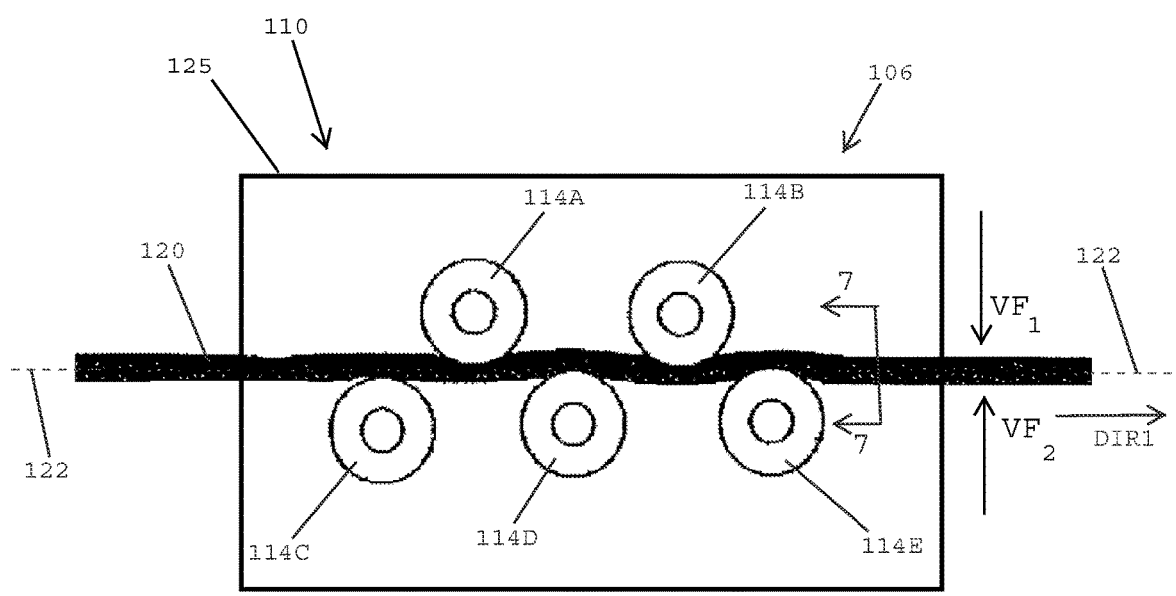
FIG. 6 is a side elevation view of the second section of the suture straightening assembly shown in FIG. 4.

Referring to FIGS. 4 and 5, in one embodiment, the first straightening section 108 preferably includes a series of free-wheeling rollers 112A-112E that preferably lie in a horizontal plane. Referring to FIGS. 4 and 6, in one embodiment, the second straightening section 110 desirably includes free-wheeling rollers 114A-114E that lie within a vertical plane that is perpendicular to the horizontal plane of the rollers 112A-112E (FIG. 5) of the first straightening section 108. Referring to FIGS. 4-6, in one embodiment, as a suture is drawn from a suture channel 104 (FIG. 3) for being dispensed from the suture package 100 (FIG. 3), the suture thread 120 is pulled along a suture dispensing path 122 in the direction designated DIR1. As the suture is dispensed, the suture thread 120 is first pulled through the first set of rollers 112A-112E of the first straightening section 108, and is then pulled through the second set of rollers 114A-114E of the second straightening section 110 for flexing the suture 120 within both a first plane (e.g., a horizontal plane) and second plane (e.g., a vertical plane) that is perpendicular to the first plane, thereby removing any bends or loops that may be present in the suture thread 120.

In one embodiment, as a suture thread 120 is pulled along a suture dispensing path 122 in the direction designated DIR1, the suture thread 120 is preferably flexed in opposite directions within a first plane (e.g., a horizontal plane) by the rollers of the first straightening section 108, and the suture thread may then be flexed in opposite directions within a second plane (e.g., a vertical plane) by the rollers of the second straightening section 110. The opposing rollers preferably flex the suture in opposite directions within both the first plane and the second plane for removing any bends or loops that may be present in the suture thread 120 for straightening the suture thread for use during a suturing operation.

FIG. 5 is a top plan view of the first straightening section 108 of the suture straightening assembly shown in FIG. 4. The first straightening section 108 preferably includes first rollers 112A-112C that are located on a first lateral side of the suture thread 120 and opposing or adjacent second rollers 112D-112E that are located on a second lateral side of the suture thread 120. As the suture thread 120 is pulled and/or drawn along the suture dispensing path 122 in the direction designated DIR1, the suture thread 120 preferably passes between the opposing rollers 112A-112C and 112D-112E for flexing the suture 120 in opposite directions within the first plane (e.g., a horizontal plane). In one embodiment, the first rollers 112A-1120 apply a first horizontal flexing force $HF_1$ to a first lateral side of the suture thread 120 and the second rollers 112D-112E apply a second horizontal flexing force $HF_2$ to a second lateral side of the suture thread 120 for flexing the suture thread in two opposite directions within a horizontal plane. In one embodiment, the distance between the first rollers 112A-1120 on the first lateral side of the suture thread 120 and the second rollers 112D-112E on the second lateral side of the suture thread is desirably less than the outer diameter of the suture thread 120 for insuring bi-directional flexing of the suture thread as it passes between the opposing first rollers 112A-112C and second rollers 112D-112E.

FIG. 6 shows a side elevation view of the second straightening section 110 of the suture straightening assembly 106 shown in FIG. 4. The second straightening section 110 preferably includes first rollers 114A-1148 located on a top side of the suture thread 120 and second rollers 1140-114E located on a bottom side of the suture thread 120. The first and second rollers 114A-114B and 114C-114E are preferably located on opposite sides of the suture thread 120 for providing opposing flexing forces on the top and bottom sides of the suture thread 120. In one embodiment, as the suture thread 120 is pulled along the suture dispensing path 122 in the direction designated DIR1, the suture thread 120 preferably passes between the opposing rollers 114A-114B and 1140-114E for being flexed in opposite directions within a second plane (e.g., a vertical plane). In one embodiment, the first rollers 114A-114B apply a first vertical flexing force $VF_1$ to a top side of the suture thread 120 and the second rollers 114C-114E apply a second vertical flexing force $VF_2$ to a bottom side of the suture thread 120 for flexing the suture thread in two opposite directions within a vertical plane.

In one embodiment, the first straightening section 108 of the suture straightening assembly is adjacent the second straightening section 110 of the suture straightening assembly. In one embodiment, the second straightening section 110 may be located downstream of the first straightening section 108. In another embodiment, the second straightening section 110 may be located upstream of the first straightening section 108.

Referring to FIGS. 5 and 6, in one embodiment, the first set of rollers of the first straightening section 108 is mounted on a first carriage 115 that aligns the rollers 112A-112E (FIG. 5) of the first set of rollers with the first plane, and the second set of rollers of the second straightening section 110 is mounted on a second carriage 125 that aligns the rollers 114A-114E (FIG. 6) of the second set of rollers with the second plane.

Figure 7:
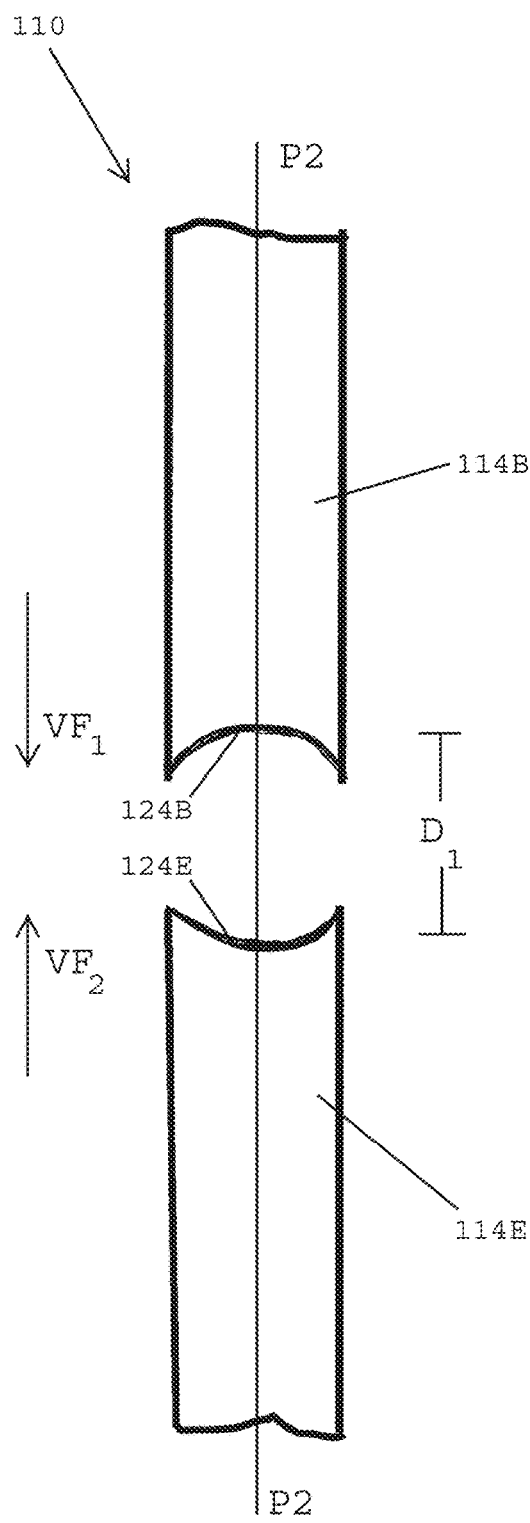
FIG. 7 is an end view of two opposing rollers of the second section of the suture straightening assembly shown in FIG. 6, in accordance with one embodiment of the present patent application.
Figure 8:
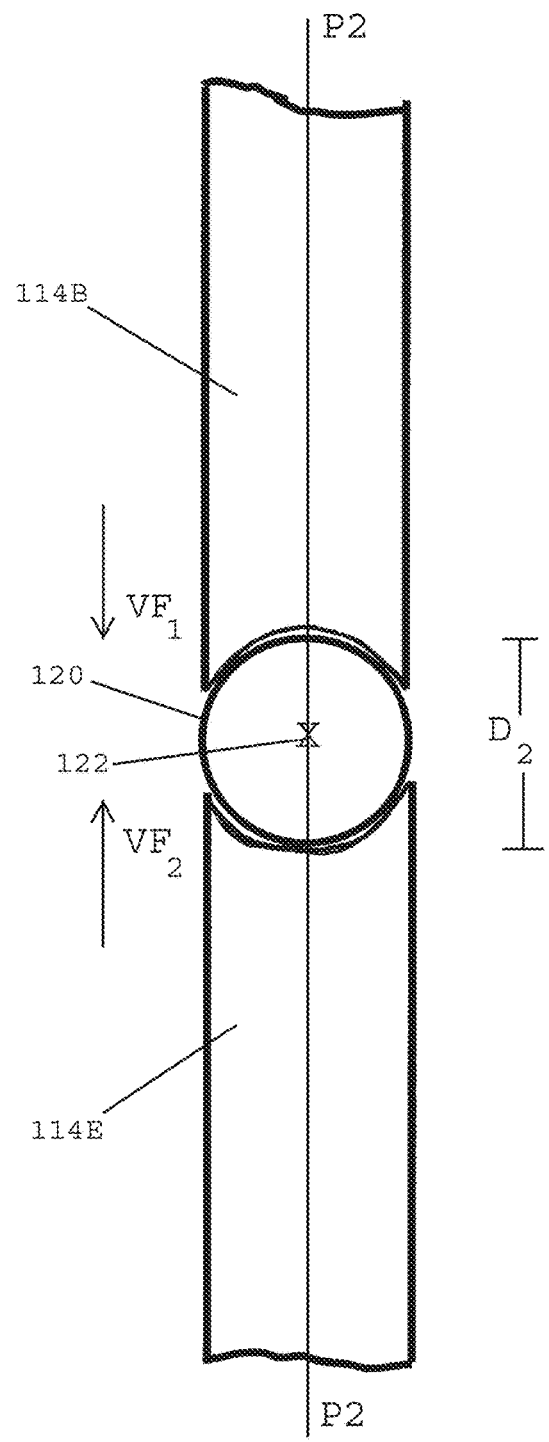
FIG. 8 shows the two opposing rollers of FIG. 7 applying flexing forces to an outer surface of a suture being drawn between the two opposing rollers, in accordance with one embodiment of the present patent application.

Referring to FIGS. 7 and 8, in one embodiment, the second straightening section 110 may include a first roller 114B that is configured to overlie a top side of a suture thread, and an opposing or adjacent second roller 114E that is configured to underlie a bottom side of the suture thread.

In one embodiment, the first and second rollers 114B, 114E preferably oppose one another and lie within a plane designated P2 (e.g., a vertical plane). In one embodiment, the first roller 114 has an outer perimeter having a concave-shaped surface 124B that is adapted to engage an outer surface of a suture thread (e.g., on a top side of the suture thread), and the opposing, second roller 114E has an outer perimeter having a concave-shaped surface 124E that is adapted to engage an outer surface of the suture thread (e.g., on an underside of the suture thread). In one embodiment, the opposing concave-shaped surfaces 124B, 124E define a distance $D_1$ that is less than the outer diameter of a suture thread that is drawn between the opposing rollers 114B, 114E. In one embodiment, the distance $D_1$ between the opposing rollers of the second straightening section 110 is desirably less than the outer diameter $D_2$ of the suture thread 120 for insuring bi-directional flexing of the suture thread as it passes between the opposing rollers. In one embodiment, as a suture is pulled between the concave surfaces 124B, 124E of the opposing rollers 114B, 114E, the concave surface 124B of the upper roller 114B provides a downward flexing force $VF_1$ and the concave surface 124E of the lower roller 114E provides an upward flexing force $VF_2$. The opposing flexing forces VF1 and VF2 are preferably applied within the plane P2 (e.g., a vertical plane) for flexing a suture thread in two opposite directions within the plane P2.

Referring to FIGS. 7 and 8, when a suture thread 120 is pulled and/or drawn along the suture dispensing path 122 between the opposing rollers 114B, 114E (for removing the suture thread from the suture package), the opposing concave surfaces 1248, 124E of the rollers desirably engage the respective top and bottom sides of the suture thread 120. In one embodiment, the outer diameter $D_2$ of the suture thread 120 is preferably larger than the distance $D_1$ (FIG. 7) between the opposing concave surfaces 124B, 124E of the opposing rollers 1148, 114E. As a result, the opposing rollers apply flexing forces VF1 and VF2 to the respective top and bottom surfaces of the suture thread 120 for flexing the suture thread in two opposite directions within the plane designated P2.

FIG. 9A illustrates the horizontal flexing forces that may be applied to the lateral sides of the suture thread 120 as the suture thread is pulled through the first straightening section 108, The first set of rollers 112A-112C (FIG. 5) exert a horizontal force designated HF, and the second set of rollers 112D-112E (FIG. 5) exert an opposing horizontal force $HF_2$. The opposing forces $HF_1$ and $HF_2$ are preferably applied within a horizontal plane P1.

FIG. 9B illustrates the vertical flexing forces that may be applied to the top and bottom sides of the suture thread 120 as the suture thread is pulled through the second straightening section 110, The first set of rollers 114A-114B (FIG. 6) exert a vertical force in a direction $VF_1$ and the second set of rollers 114C-114E exert an opposing vertical force in the direction designated $VF_2$. The opposing forces $VF_1$ and VF, preferably applied within a vertical plane P2.

Referring to FIGS. 10A-10C, in one embodiment, a suture straightening assembly may apply flexing forces in more than two planes. In one embodiment, a suture straightening assembly includes a first station 208 (FIG. 10A) having rollers that apply opposing flexing forces $HF_1$ and $HF_2$ within a horizontal plane HP, a second station 209 (FIG. 10B) having rollers that apply opposing flexing forces $DF_1$ and $DF_2$ within a diagonal plane DP that defines an angle with the horizontal plane HP of the first section 208, and a third station 210 (FIG. 10O) having rollers that apply opposing flexing forces $VF_1$ and $VF_2$ within a vertical plane VP that is perpendicular to the horizontal plane HP (FIG. 10A) and that defines an angle with the diagonal plane DP of the second station 209 (FIG. 10B).

Figure 11:
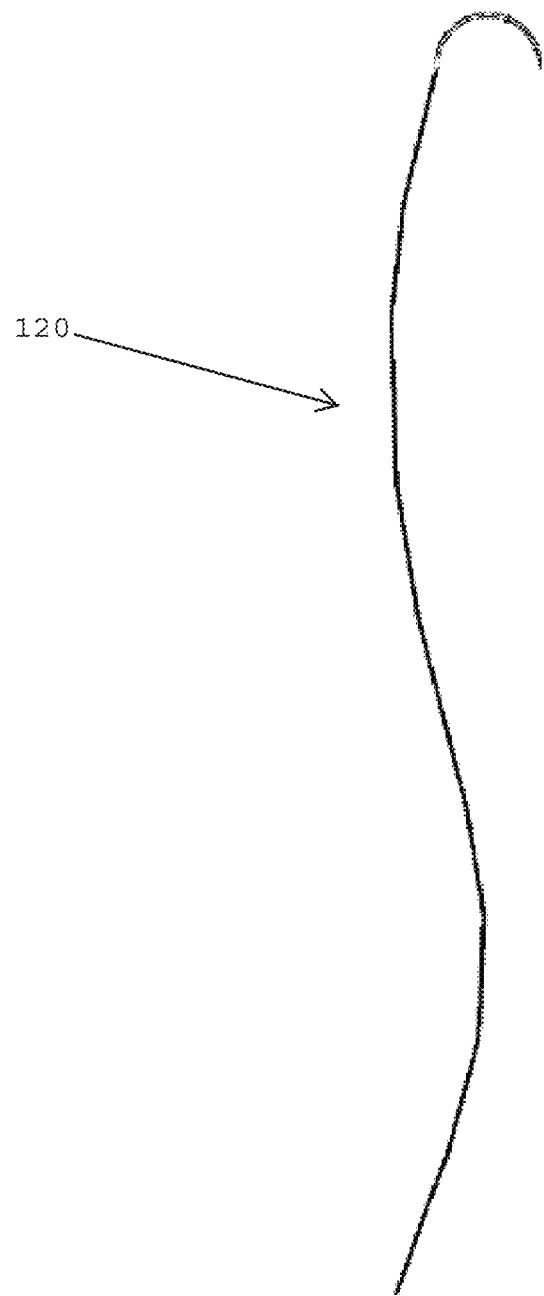
FIG. 11 is a perspective view of a suture including a suture thread and a needle secured to the suture thread after the suture thread has been drawn through the suture straightening assembly of FIG. 4, in accordance with one embodiment of the present patent application.

Referring to FIG. 11, in one embodiment, after the suture thread 120 has been drawn through the suture straightening assembly shown and described herein, the suture thread 120 is substantially straight because any bends or loops that were present in the suture thread have been removed by the rollers of the suture straightening assembly 106 (FIGS. 3 and 4).

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A suture package comprising:
  a suture housing;
  a suture disposed on said suture housing, wherein said suture includes a suture thread having an outer diameter;
  a suture straightening assembly provided on said suture housing, said suture straightening assembly defining a suture dispensing path for removing said suture thread from said suture housing;
  said suture straightening assembly including a first straightening section that is configured to apply first bi-directional flexing forces upon an exterior surface of said suture thread within a first plane as said suture thread is drawn along the suture dispensing path, and a second straightening section that is configured to apply second bi-directional flexing forces upon the exterior surface of said suture thread within a second plane as said suture thread is drawn along the suture dispensing path, wherein said first and second planes extend along axes that define an angle relative to one another;
  wherein said first straightening section comprises a first set of rollers configured to apply the first bi-directional flexing forces upon the exterior surface of said suture thread, said first set of rollers including a series of first rollers located on a first side of said suture thread and an opposing series of second rollers located on a second side of said suture thread that are configured to simultaneously apply the first bi-directional flexing forces upon the exterior surface of said suture thread, wherein each of said rollers of said first straightening section includes an outer perimeter having a concave-shaped surface that is adapted to engage the exterior surface of said suture thread, and wherein the opposing concave-shaped surfaces of said opposing first and second series of rollers of said first straightening section define a first distance that is less than the outer diameter of said suture thread.

2. The suture package as claimed in claim 1, wherein said first and second planes are perpendicular to one another.

3. The suture package as claimed in claim 1, wherein one of said first and second planes is a horizontal plane and the other of said first and second planes is a vertical plane.

4. The suture package as claimed in claim 1, wherein said second straightening section comprises a second set of rollers that is configured to apply the second bi-directional flexing forces upon the exterior surface of said suture thread within said second plane as said suture thread is drawn along the suture dispensing path, said second set of rollers including a series of first rollers located above said suture thread and an opposing series of second rollers located below said suture thread that are configured to simultaneously apply the second bi-directional flexing forces upon the exterior surface of said suture thread, wherein each of said rollers of said second straightening assembly includes an outer perimeter having a concave-shaped surface that is adapted to engage the exterior surface of said suture thread, and wherein the opposing concave-shaped surfaces of said opposing first and second series of rollers of said second straightening section define the first distance that is less than the outer diameter of said suture thread.

5. The suture package as claimed in claim 4, wherein said rollers of said first straightening section are located on opposite lateral sides of the suture dispensing path and said rollers of said second straightening section are located above and below the suture dispensing path.

6. The suture package as claimed in claim 4, wherein said suture straightening assembly is mounted on said suture housing and has a suture thread inlet and a suture thread outlet, and wherein said first and second straightening sections are located between the suture thread inlet and the suture thread outlet of said suture straightening assembly.

7. The suture package as claimed in claim 6, wherein said first and second straightening sections are adjacent to one another within said suture straightening assembly.

8. The suture package as claimed in claim 7, wherein said first straightening section is closer to the suture thread inlet of said suture straightening assembly than said second suture straightening section.

9. The suture package as claimed in claim 7, wherein said first suture straightening section is closer to the suture threads outlet of said suture straightening assembly than said second straightening section.

10. The suture package as claimed in claim 4, wherein said first rollers of said first straightening section are mounted on a first carriage that aligns said rollers of said first straightening section with said first plane, and wherein said rollers of said second straightening section are mounted on a second carriage that aligns said rollers of said second straightening section with said second plane.

11. The suture package as claimed in claim 1, wherein said suture comprises a needle secured to an end of said suture thread, and wherein said suture housing comprises a tray including a suture channel for said suture thread and a needle park that engages said needle for securing said needle to said tray.

12. A suture package comprising:
a suture housing including a tray having a suture channel;
at least one suture disposed on said suture housing, wherein said at least one suture includes a suture thread disposed within said suture channel of said tray;
a suture straightening assembly provided on said suture housing, said suture straightening assembly defining a suture dispensing path for removing said suture thread from said suture housing;
said suture straightening assembly including a first suture thread straightening section that is configured to apply first bi-directional flexing forces within a first plane upon an exterior surface of said suture thread as said suture thread is drawn along the suture dispensing path, and a second suture thread straightening section that is configured to apply second bi-directional flexing forces within a second plane upon the exterior surface of said suture thread as said suture thread is drawn along the suture dispensing path, wherein said first and second planes extend along axes that define an angle relative to one another;
wherein said first suture thread straightening section comprises a first set of rollers configured to apply the first bi-directional flexing forces upon the exterior surface of said suture thread, said first set of rollers including a series of first rollers located on a first side of said suture thread and an opposing series of second rollers located on a second side of said suture thread that are configured to simultaneously apply the first bi-directional flexing forces in two opposite directions within said first plane, wherein each of said rollers of said first suture thread straightening section includes an outer perimeter having a concave-shaped surface that is adapted to engage the exterior surface of said suture thread, and wherein the opposing concave-shaped surfaces of said opposing first and second series of rollers of said first suture thread straightening assembly define a first distance that is less than the outer diameter of said suture thread.

13. The suture package as claimed in claim 12, wherein said second suture thread straightening section comprises a second set of rollers that is configured to apply the second bi-directional flexing forces within said second plane upon the exterior surface of said suture thread as said suture thread is drawn along the suture dispensing path, wherein said first and second planes extend along axes that define an angle relative to one another, said second set of rollers including a series of first rollers located above said suture thread and an opposing series of second rollers located below said suture thread that are configured to simultaneously apply the second bi-directional flexing forces in two opposite directions within said second plane, wherein each of said rollers of said second suture thread straightening section includes an outer perimeter having a concave-shaped surface that is adapted to engage the exterior surface of said suture thread, and wherein the opposing concave-shaped surfaces of said opposing first and second series of rollers of said second suture thread straightening section define the first distance that is less than the outer diameter of said suture thread.

14. The suture package as claimed in claim 13, wherein the first bi-directional flexing forces applied by said rollers of said first suture thread straightening section flex said suture thread in the two opposite directions within said first plane, and wherein the second bi-directional flexing forces applied by said rollers of said second suture thread straightening section flex said suture thread in the two opposite directions within said second plane.

15. The suture package as claimed in claim 13, wherein said rollers of said first suture thread straightening section are located on opposite lateral sides of the suture dispensing path and said rollers of said second suture thread straightening section are located above and below the suture dispensing path.

16. The suture package as claimed in claim 15, wherein said rollers of said first suture thread straightening section are mounted on a first carriage that aligns said rollers of said first suture thread straightening section with the said first plane, and wherein said rollers of said second suture thread straightening section are mounted on a second carriage that aligns said rollers of said second suture thread straightening section with the said second plane.

17. The suture package as claimed in claim 12, wherein said suture thread disposed within said suture channel has a curved configuration, wherein a needle is secured to an end of said suture thread, and wherein said tray includes a needle park for securing said needle to said suture housing.

18. A suture package comprising:
  a suture housing including a tray having a suture channel and a needle park;
  at least one suture disposed on said suture housing, wherein said at least one suture includes a suture thread disposed within said suture channel of said tray and a needle secured to an end of said suture thread that is secured to said tray at said needle park;
  a suture straightening assembly provided on said suture housing, said suture straightening assembly defining a suture dispensing path for removing said suture thread from said tray of said suture housing;
  said suture straightening assembly including a first suture thread straightening section that is configured to apply first bi-directional flexing forces within a first plane upon an exterior surface of said suture thread as said suture thread is drawn along the suture dispensing path, and a second suture thread straightening section that is configured to apply second bi-directional flexing forces within a second plane upon the exterior surface of said suture thread as said suture thread is drawn along the suture dispensing path, wherein said first and second suture thread straightening sections are adjacent to one another within said suture straightening assembly, and wherein said first and second planes extend along axes that define an angle relative to one another;
  said first suture thread straightening section comprising a first set of rollers configured to apply said first bi-directional flexing forces upon the exterior surface of said suture thread, said first set of rollers including a series of first rollers located on a first side of said suture thread and an opposing series of second rollers located on a second side of said suture thread that are configured to simultaneously apply the first bi-directional flexible forces within said first plane, wherein each of said rollers of said first suture thread straightening section includes an outer perimeter having a concave-shaped surface that is adapted to engage the exterior surface of said suture thread, and wherein the opposing concave-shaped surfaces of said opposing first and second series of rollers of said first suture thread straightening section define a first distance that is less than an outer diameter of said suture thread.

19. The suture package as claimed in claim 18, wherein one of said first and second planes is a horizontal plane and the other one of said first and second planes is a vertical plane that is perpendicular to the horizontal plane.

20. The suture package as claimed in claim 18, wherein said first bi-directional flexing forces applied by said first suture thread straightening section simultaneously flexes said suture thread in two opposite directions within said first plane, and wherein said second suture thread straightening section simultaneously flexes said suture thread in two opposite directions within said second plane.

21. The suture package as claimed in claim 18, wherein said second suture thread straightening section comprises a second set of rollers that is configured to apply said second bi-directional flexing forces upon the exterior surface of said suture thread, said second set of rollers including a series of first rollers located above said suture thread and an opposing series of second rollers located below said suture thread that are configured to simultaneously apply the second bi-directional flexible forces within said second plane, wherein each of said rollers of second suture thread straightening section includes an outer perimeter having a concave-shaped surface that is adapted to engage the exterior surface of said suture thread, and wherein the opposing concave-shaped surfaces of said opposing rollers of said second suture thread straightening section define the first distance that is less than the outer diameter of said suture thread.

22. The suture package as claimed in claim 1, wherein the opposing concave-shaped surfaces of said opposing first and second series of rollers of said first straightening section are concavely curved.

23. The suture package as claimed in claim 4, wherein the opposing concave-shaped surfaces of said opposing first and second series of rollers of said second straightening section are concavely curved.

* * * * *